United States Patent
Ihrig et al.

(12) 
(10) Patent No.: US 6,222,075 B1
(45) Date of Patent: Apr. 24, 2001

(54) PROCESS FOR THE PRODUCTION OF N, N, N', N',-TETRA-(2-HYDROXYETHYL) ETHYLENE DIAMINE

(75) Inventors: Klaus Ihrig, Waldbrunn-Schollbrunn; Manfred Bergfeld, Erlenbach-Mechenhard; Christian Blaufelder, Obernburg, all of (DE)

(73) Assignee: Akzo Nobel NV, Arnhem (NL)

( * ) Notice: Subject to any disclaimer, the term of this patent is extended or adjusted under 35 U.S.C. 154(b) by 0 days.

(21) Appl. No.: 09/331,048

(22) PCT Filed: Feb. 21, 1998

(86) PCT No.: PCT/EP98/01008

§ 371 Date: Jul. 8, 1999

§ 102(e) Date: Jul. 8, 1999

(87) PCT Pub. No.: WO98/38153

PCT Pub. Date: Sep. 3, 1998

(30) Foreign Application Priority Data

Feb. 27, 1997 (DE) .............................................. 197 07 872

(51) Int. Cl.⁷ .................................................. C07C 213/00
(52) U.S. Cl. ............................................................. 564/475
(58) Field of Search ............................................... 564/475

(56) References Cited

U.S. PATENT DOCUMENTS 2,884,459 4/1959 Kirkpatrick et al. .
5,846,453 12/1998 Mohr et al. .

FOREIGN PATENT DOCUMENTS

1020347 * 12/1957 (DE) .
44 35 688 A1 4/1996 (DE) .
WO 90/03964 4/1990 (WO) .

OTHER PUBLICATIONS

Chem. Abstracts, vol. 35, No. 1, 1941.*
Chemical Abstracts, vol. 35, No. 1, XP–002064711, 1941.

* cited by examiner

*Primary Examiner*—Samuel Barts
(74) *Attorney, Agent, or Firm*—Oliff & Berridge, PLC

(57) ABSTRACT

A process is described for the production of N,N,N',N'-tetra-(2-hydroxyethyl)-ethylene diamine in a solvent, in which ethylene diamine is reacted selectively with ethylene oxide in the absence of water in one or more saturated $C_3$–$C_9$ alcohols at a temperature from 120 to 220° C. and at a pressure from 2 to 60 bar in a molar ratio of 1:4, with a high yield. The conversion is preferably carried out in isopropanol, isomeric $C_7$–$C_9$ alcohol mixtures, $C_8$ alcohol mixtures or $C_9$ alcohol mixtures at a temperature from 140 to 180° C.

18 Claims, 2 Drawing Sheets

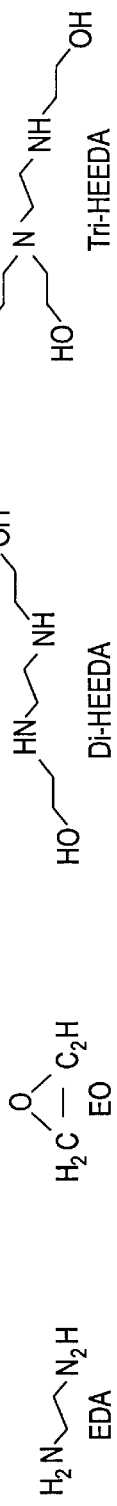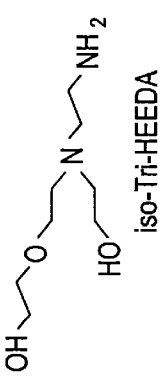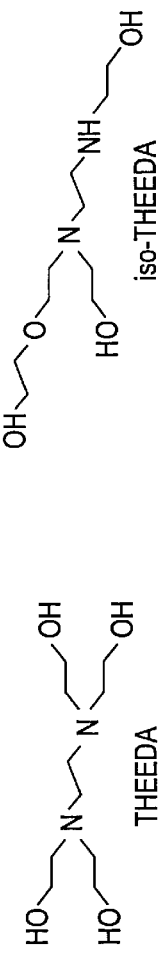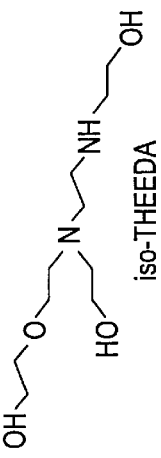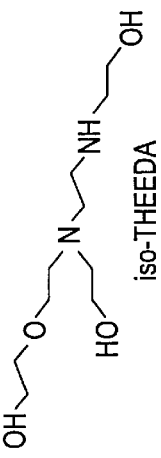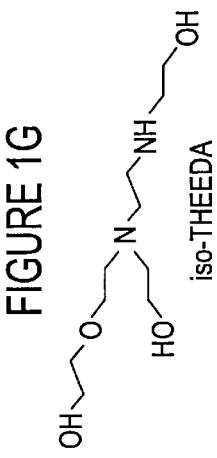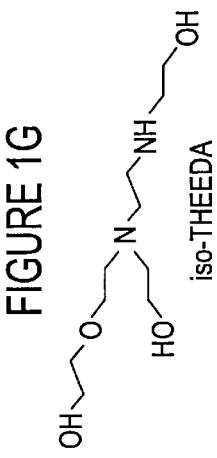

PROCESS FOR THE PRODUCTION OF N, N, N', N',-TETRA-(2-HYDROXYETHYL) ETHYLENE DIAMINE

This application is a 371 of PCT/EP98/01008 filed Feb. 21, 1998.

DESCRIPTION

The invention relates to a process for the production of N,N,N',N'-tetra-(2-hydroxyethyl)-ethylene diamine (=THEEDA) by reacting ethylene diamine with ethylene oxide in a solvent.

A method is known from publication DE-AS 1 020 347, in which alkylene diamines with between 2 and 6 carbon atoms, e.g., ethylene diamine, are reacted with propylene oxide in the presence of water or an alcohol as a conversion catalyst at a temperature of between 40 and 200° C. and preferably between 40 and 120° C., in a molar ratio of 1:4. The reaction produces almost quantitative yields, and these are not even dependent on whether an excess of propylene oxide has been used or not, since the tetraoxypropylated alkylene diamines do not react further with excess propylene oxide under the specified reaction conditions.

In publication DE-AS 1 020 347, it is emphasised that unlike tetraoxypropylated ethylene diamine, the N,N,N',N'-tetra-(2-hydroxyethyl)-ethylene diamine produced by Sherlin and others in accordance with Chemical Abstracts 35, 5858 (1941) decomposes on heating and cannot be distilled. The production of this product, which is, however, encumbered with diverse by-products, is carried out here by leaving ethylene diamine and ethylene oxide to stand in an aqueous solution for four hours and then removing the water by vacuum. The reaction products have the consistency of a thick oil.

BRIEF DESCRIPTION OF DRAWINGS

It is a fact that in comparison with ethylene diamine, ethylene oxide lacks good selectivity under a wide range of reaction conditions in the formation of tetraoxyethylated ethylene diamine, which, on the contrary, propylene oxide shows in the reaction to form tetraoxypropylated ethylene diamine.

FIG. 1 shows from extensive research work which led to the present invention, that, for example, under the conditions of publication DE-AS 1 020 347, not only THEEDA but also a number of possible by-products are formed, which range from dioxyethylated ethylene diamine (=di-HEEDA) to ethylamino ethanol (=EAE) and methyldiethanol amine (=MDEA).

Figure 2:
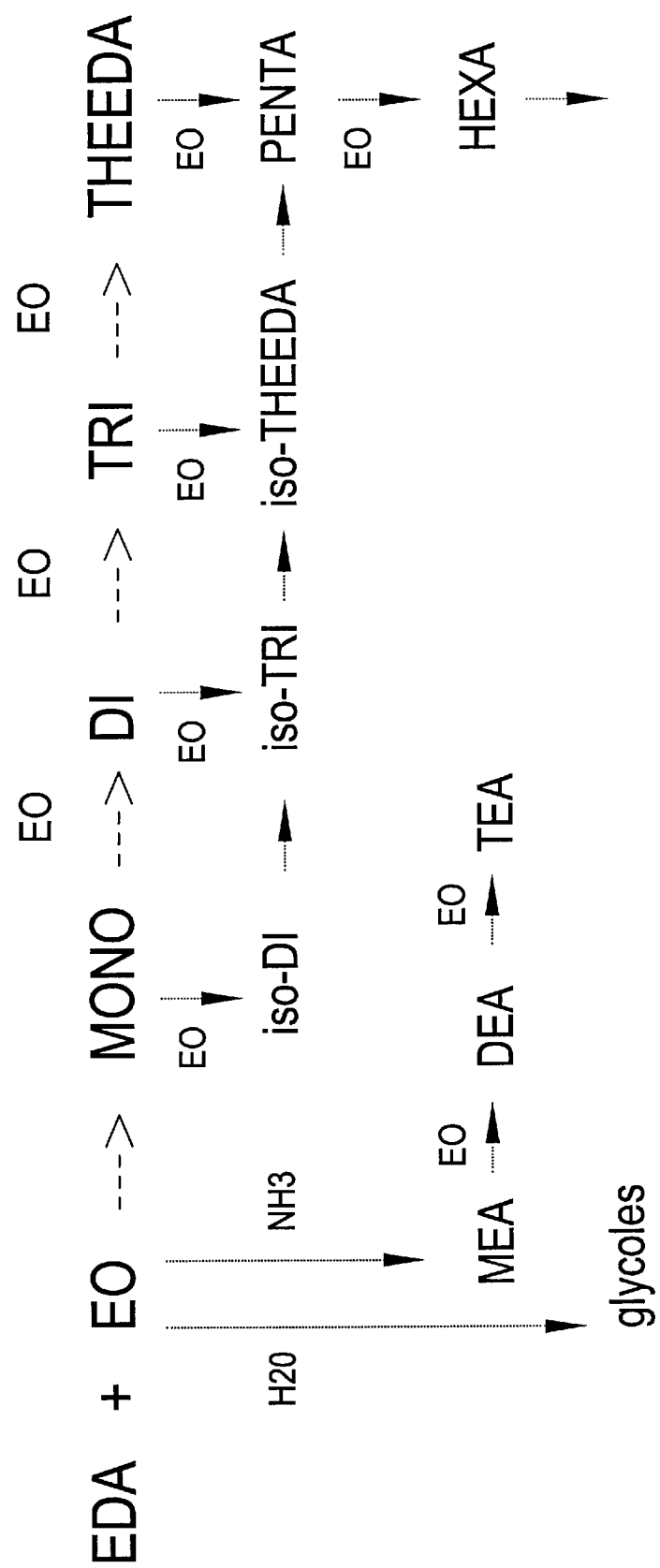
FIG. 2 summarises in diagrammatic form the reaction paths to each of the by-products and the desired product THEEDA.

Surprisingly, the action of ethylene oxide (=EO) on ethylene diamine (=EDA) causes cleavage of ammonia, which on reaction with EO forms monoethanol amine (=MEA), diethanol amine (=DEA) and triethanol amine (=TEA). If water is present, the glycols ethylene glycol, diethylene glycol and triethylene glycol are also produced as by-products of the EO conversion.

The feasibility of an economical industrial-scale process for the production of N,N,N',N'-tetra-(2-hydroxyethyl)-ethylene diamine depends, in accordance with FIG. 2, on whether reaction conditions exist which greatly favour the main reaction of ethylene diamine with ethylene oxide via mono-HEEDA (=N-mono(2-hydroxyethyl)-ethylene diamine), di-HEEDA (=N,N-di-(2-hydroxyethyl)-ethylene diamine) or N,N'-di(2-hydroxyethyl)-ethylene diamine and tri-HEEDA (=N,N,N'-tri-(2-hydroxyethyl)-ethylene diamine) to THEEDA (note that in line 1 of FIG. 2 the first three compounds just mentioned are abbreviated to MONO, DI and TRI). At the same time, this means that the possible secondary reactions shown in FIG. 2, which lead either via THEEDA or via the iso-compounds iso-di-HEEDA, iso-tri-HEEDA (abbreviated to iso-DI and iso-TRI in line 2 of FIG. 2) and iso-THEEDA to penta-HEEDA and hexa-HEEDA (abbreviated to PENTA and HEXA at the right of FIG. 2), must be practically avoided.

The object of the present invention is therefore to provide an economical technical process for the production of N,N,N',N'tetra-(2-hydroxyethyl)-ethylene diamine (=THEEDA) in a solvent, in which the starting components ethylene oxide and ethylene diamine have a high selectivity for the formation of THEEDA and consequently in which the presence of subethoxylated and superethoxylated tetra-HEEDA derivatives such as tri-HEEDA, penta-HEEDA and hexa-HEEDA, and the presence of mono, di and triethanolamine is practically avoided. The required high selectivity is therefore of decisive importance, since the specified by-products cannot be separated from the required end product, or cannot be separated economically from the required end product and therefore impair the quality of the product.

It has now been found that it is possible to produce THEEDA with high yields and selectivity by reacting ethylene diamine with ethylene oxide in the absence of water in one or more saturated $C_3$–$C_9$ alcohols at a temperature from 120 to 220° C. and at a pressure from 2 to 60 bar in a molar ratio of 1:4.

Unlike the oxypropylation of ethylene diamine discussed above, in which the presence of water is indeed desirable, the use of water as a solvent would be associated with an unacceptable yield loss in the corresponding oxyethylation process. Water causes hydrolysis of the end product THEEDA, and in particular an undesirable amount of triethanolamine is produced as a by-product. As the comparative example 3 also shows, a THEEDA yield of just 63% is achieved when water is used as a solvent at a reaction temperature of 140° C. The use of lower alcohols, such as methanol and ethanol, also prevents the required high selectivity, as illustrated in comparative examples 4 and 5. The same results are found when higher alcohols from $C_{10}$ are used (see comparative example 6).

The organic solvents of the present invention are saturated $C_3$ to $C_9$ alcohols. Some examples are: n-propanol, isopropyl alcohol, n-butanol, isobutyl alcohol, tert.-butyl alcohol, 1-pentanol, 2-methyl-1-butanol, 3-methyl-1-butanol, 2,2-dimethyl-1-propanol, 1-hexanol, 2-methyl-1-pentanol, 2-ethyl-1-butanol, 4-methyl-2-pentanol, 1-heptanol, 3-methyl-1-hexanol, 2-methyl-2-hexanol, 1-octanol, 2-octanol, 2-ethyl-1-hexanol, 3,3-dimethyl-1-hexanol, 3,5-dimethyl-1-hexanol, 4,5-dimethyl-1-hexanol, 3-methyl-1-heptanol,5-methyl-1-heptanol, 1-nonanol, 2,6-dimethyl-4-heptanol, 3,5,5-trimethyl-1-hexanol and cyclohexanol. The use of isopropyl alcohol, as a low alcohol which is free from isomers, is particularly favoured.

Higher alcohols, from the $C_{10}$ alcohols upwards, also prevent a high selectivity, as do the more polar low alcohols mentioned above or very polar or absolutely non-polar solvents, such as cyclohexane and diethyl ether. It is also absolutely possible to use mixtures of saturated $C_3$ to $C_9$ alcohols for the production of THEEDA. These mixtures can, in principle, contain any substances and percentage compositions from the entire range of saturated $C_3$–$C_9$ alcohols. For the purposes of the invention, therefore, the alcohol mixtures in question are regarded as one solvent. The use of alcohol mixtures is particularly advantageous when higher alcohols are used, because of the existing isomerism ratios. Starting as low as the $C_5$ alcohols, the use of isomer mixtures of amyl alcohols, for example as they are obtained by oxo synthesis, is preferred to each isomer-free $C_5$ alcohol, also for economical reasons. The oxo alcohols are made up entirely of primary alcohols. The alcohol mixture obtained from the hydroformylation and hydrogenation of n-butene contains approximately two thirds 1-pentanol and one third 2-methyl-1-butanol as well as small quantities of 3-methyl-1-butanol. This is commercially available under the name "amyl alcohol" or "primary amyl alcohol".

The use of $C_7$–$C_9$ alcohol mixtures as a solvent is also preferred. These are mixtures of the C-numbers 7 and 8 or 7 to 9, which are produced from straight-chain olefin cuts by means of oxo synthesis. They are available under the names Oxanol 78 (Ruhrchemie) and Alphanol 79 (ICI, Shell). Oxanol 78 is made up of approximately 70–75% $C_7$ alcohols and 30–25% $C_8$ alcohols. The proportion of straight-chain alcohols is approximately 60–65%, while the remaining 35–40% consist primarily of methyl branched alcohols. Alphanol 79 is an alcohol mixture with approximately 45% $C_7$ alcohols, 43% $C_8$ alcohols and 12% $C_9$ alcohols.

Isomeric $C_8$ alcohol mixtures obtained by means of hydroformylation of pure heptenes or suitable heptene fractions, which are usually obtained by means of mixed dimerisation of butene and propene, and isomeric $C_9$ alcohol mixtures, which are produced by dimerisation or mixed dimerisation of butene and isobutene followed by hydroformylation of the $C_8$ olefins, are also preferred solvent mixtures in the framework of the present invention. The purity of these alcohol mixtures should always be>99%.

Further important features of the present invention are the temperature range from 120 to 220° C. and the pressure range from 2 to 60 bar, which are required for high selectivity. It has been found that preferred low temperatures, for example, from 70 to 100° C. used in the oxypropylation of ethylene diamine (see the examples in publication DE-AS 1 020 347) in the oxyethylation of ethylene diamine result in yields which are too low and high quantities of tri-HEEDA, penta-HEEDA and hexa-HEEDA. This is illustrated by comparative examples 1 and 2. In the scope of the present invention, a temperature range from 140 to 180° C. is preferred.

The molar ratio of ethylene diamine to ethylene oxide of 1:4 must be maintained very accurately in the oxyethylation of ethylene diamine, in contrast to the oxypropylation of ethylene diamine. While an excess of propylene oxide is quite harmless in the oxypropylation of ethylene diamine, and does not cause the formation of undesirable higher oligomers, comparative examples 7 and 8 show exactly the opposite phenomenon in the oxyethylation of ethylene diamine. An excess of ethylene oxide as low as 5% causes the yield of THEEDA to drop to 92.2%, due to the formation of corresponding amounts of penta-HEEDA and TEA. If a 5% deficit of ethylene oxide is used, the yield of THEEDA drops to 90.5%, due to the formation of greater amounts of tri-HEEDA.

Generally, the $C_3$–$C_9$ alcohol or alcohols and the ethylene diamine are placed in the reaction vessel first, and the reaction chamber is flushed with nitrogen and heated to the reaction temperature, upon which the ethylene oxide is then added. The dosage time of the ethylene oxide can be varied within a wide range. This time is generally from 5 to 60 minutes, whereby an ethylene oxide dosage time from 15 to 25 minutes is generally preferred.

The amount of $C_3$–$C_9$ alcohol or alcohols can also be varied within wide limits. Very high amounts of $C_3$–$C_9$ alcohol or alcohols lead to even higher selectivities, but also to large apparatus volumes, which makes the process more expensive. Very low amounts of $C_3$–$C_9$ alcohol or alcohols lower the selectivity again somewhat and can cause problems with the dissipation of heat, so that it may be necessary to use cooling facilities or apparatus constructions which can be expensive. It has proven advantageous to select the amount of $C_3$–$C_9$ alcohol or alcohols so that the THEEDA concentration after conversion is from 5 to 60% and preferably from 20 to 40%.

Because of the relatively high reaction times, which are typical for ethoxylation reactions, the process of the invention is also excellently suited for continuous-process production in a tubular-flow reactor or in a cascade of stirred-tank reactors. Because of the efficient reaction system, just a small reactor volume is required here in order to bring about complete conversion of the ethylene diamine into tetra-HEEDA. A cascade of stirred-tank reactors is particularly suitable for use with high product concentrations, on the one hand because the reaction heat which arises is effectively dispersed and on the other hand because the intensive premixing minimises the local concentrations of ethylene oxide.

After separation of the saturated $C_3$–$C_9$ alcohols used, for example by means of vacuum distillation, the THEEDA produced in accordance with the process of the invention is of such high quality that, unlike the prior art, it can be purified by distillation without decomposition (see Example 18). The process of the invention allows production on an industrial scale of an interesting intermediate product which, due to its symmetrical structure and reactive primary hydroxyl groups, can be used in particular for the production of hydroxyethylester-quats (softener), the production of crosslinking agents and as a modifying component in the production of polymers, such as polyesters and polyurethanes.

The invention is clarified further in the following examples:

EXAMPLE 1

0.326 kg ethylene diamine (5.42 mole) and 13.55 liters of isopropanol are placed in a 35 liter stainless-steel reactor with a stirrer and double casing (thermostat cooling/heating). The reaction chamber is flushed with nitrogen and then heated to 140° C. When the reaction temperature is reached, 0.956 kg ethylene oxide (21.68 mole) are added within 47 minutes. When the ethylene oxide dosage is complete, the temperature is maintained for another 120 minutes and the experiment then ended. After cooling, the solvent is separated from the reaction product by vacuum evaporation. The THEEDA yield was 96.3% with complete conversion.

EXAMPLE 2

13.55 liters of isopropanol are placed in a 35 liter stainless-steel reactor with a stirrer and double casing (thermostat cooling/heating). The reaction chamber is flushed with nitrogen and then heated to 140° C. When the reaction temperature is reached, 0.326 kg ethylene diamine (5.42 mole) are added within 1 minute and then 0.956 kg ethylene oxide (21.68 mole) are added within 57 minutes. When the ethylene oxide dosage is complete, the temperature is maintained for another 120 minutes and the experiment then ended. After cooling, the solvent is separated from the reaction product by vacuum evaporation. The THEEDA yield was 96.2% with complete conversion.

EXAMPLE 3

12.02 g ethylene diamine (0.2 mole) and 700 ml isopropanol are placed in a 1 liter stainless-steel Büchi-type reactor with a stirrer and double casing (thermostat cooling/heating). The reaction chamber is flushed with nitrogen and then heated to 140° C. When the reaction temperature is reached, 35.24 g ethylene oxide (0.8 mole) are added within 25 minutes. When the ethylene oxide dosage is complete, the temperature is maintained for another 120 minutes and the experiment then ended. After cooling, the solvent is separated from the reaction product by vacuum evaporation. The THEEDA yield was 97.0% with complete conversion.

EXAMPLE 4

Example 3 was repeated with two exceptions. The ethylene oxide dosage time was now 20 minutes, while the reaction time after ethylene oxide dosage was extended to 240 minutes. A THEEDA yield of 97.6% was achieved here.

EXAMPLE 5

12.02 g ethylene diamine (0.2 mole) and 500 ml isopropanol are placed in a 1 liter stainless-steel Büchi-type reactor fitted with a stirrer and double casing (thermostat cooling/heating). Here again, the reaction chamber is flushed with nitrogen and then heated to 160° C. When the reaction temperature is reached, 35.24 g ethylene oxide (0.8 mole) are added within 25 minutes. The temperature is then maintained for another 120 minutes and the experiment then ended. After cooling, the solvent is here too separated from the reaction product by vacuum evaporation. The THEEDA yield was 97.9% with complete conversion.

EXAMPLE 6

Example 5 was repeated, the only alteration being that n-propanol was used as the solvent in place of isopropanol. The THEEDA yield was 95.9%.

EXAMPLE 7

Example 5 was repeated, the only alteration being that cyclohexanol was used as the solvent in place of isopropanol. The THEEDA yield was 96.3%.

EXAMPLE 8

Example 5 was repeated, the only alteration being that tert.-butyl alcohol was used as the solvent in place of isopropanol. The THEEDA yield was 96.9%.

EXAMPLE 9

Example 5 was repeated, the only alteration being that n-butanol was used as the solvent in place of isopropanol. The THEEDA yield was 96.4%.

EXAMPLE 10

Example 5 was repeated, the only alteration being that isobutanol was used as the solvent in place of isopropanol. The THEEDA yield was 95.6%.

EXAMPLE 11

Example 5 was repeated, the only alteration being that 200 ml isopropanol were used in place of 500 ml isopropanol. The THEEDA yield was 95.9%.

EXAMPLE 12

Example 5 was repeated with two alterations. The ethylene oxide dosage time was shortened considerably from 25 minutes to 5 minutes, and the reaction time after dosage of the ethylene oxide was also shortened considerably from 120 minutes to 60 minutes. The THEEDA yield was 97.0%.

EXAMPLE 13

Example 5 was repeated, the only alteration being that the ethylene oxide dosage time of 25 minutes was extended to 63 minutes. The THEEDA yield was 96.8%.

EXAMPLE 14

Example 5 was repeated, the only alteration being that a reaction temperature of 180° C. was selected instead of 160° C. The THEEDA yield was 96.7%.

EXAMPLE 15

Example 5 was repeated, the only alteration being that a reaction temperature of 120° C. was selected instead of 160° C. The THEEDA yield was 94.8%.

EXAMPLE 16

Example 5 was repeated with two alterations. The isopropanol was replaced with the same amount in grams of 2-ethyl-1-hexanol as an organic solvent, and the ethylene oxide dosage time was 20 minutes. A THEEDA yield of 97% was achieved.

EXAMPLE 17

Example 5 was repeated with three alterations. The isopropanol was replaced with the same amount in grams of 1-nonanol. The ethylene oxide dosage time was 15 minutes and the reaction time after dosage of the ethylene oxide was 60 minutes. A THEEDA yield of 96% was achieved.

EXAMPLE 18

15 g of the reaction product from example 5 which contained 0.5 weight % triethanolamine as one of its by-products, was fractionated within 150 minutes in a bulb tube distillation apparatus. The temperatures were increased from 215° C. to 250° C. at a constant pressure of 0.01 torr. On completion of the distillation process, it was possible to separate the triethanolamine almost completely from the higher-boiling THEEDA. Decomposition of the THEEDA did not take place.

COMPARATIVE EXAMPLE 1

Example 5 was repeated with a single alteration. A reaction temperature of 80° C. was selected instead of 160° C. The THEEDA yield was 70.6%, and especially relatively large quantities of tri-HEEDA, penta-HEEDA and hexa-HEEDA were produced as by-products.

COMPARATIVE EXAMPLE 2

Example 5 was repeated with a single alteration. A reaction temperature of 100° C. was selected instead of 160°

C. The THEEDA yield was 87.8%, and especially relatively large quantities of tri-HEEDA, penta-HEEDA and hexa-HEEDA were produced as by-products.

COMPARATIVE EXAMPLE 3

Example 5 was repeated with two alterations. 500 ml water were used in place of 500 ml isopropanol, and the reaction temperature from example 1 was selected, that is, 140° C. The THEEDA yield was 63%.

COMPARATIVE EXAMPLE 4

Example 5 was repeated with two alterations. 500 ml methanol were used in place of 500 ml isopropanol, and the reaction temperature from example 1 was selected, that is, 140° C. The THEEDA yield was 79.2%.

COMPARATIVE EXAMPLE 5

Example 5 was repeated with two alterations. 500 ml ethanol were used in place of 500 ml isopropanol, and the reaction temperature from example 1 was selected, that is, 140° C. The THEEDA yield was 79.2%.

COMPARATIVE EXAMPLE 6

Example 5 was repeated with three alterations. The isopropanol was replaced with the same amount in grams of 1-decanol. The ethylene oxide dosage time was 15 minutes and the reaction time after dosage of the ethylene oxide was 60 minutes. A THEEDA yield of just 90% was achieved and considerably increased amounts of TEA and higher oligomers, such as hexa-HEEDA were detected in the product.

COMPARATIVE EXAMPLE 7

Example 5 was repeated with one alteration. 37.0 g or 0.84 mole of ethylene oxide were now used in place of 35.24 g or 0.8 mole of ethylene oxide, i.e., a 5% excess of ethylene oxide. The THEEDA yield was 92.2% and in particular relatively large amounts of penta-HEEDA and TEA (triethanolamine) were produced as by-products.

COMPARATIVE EXAMPLE 8

Example 5 was repeated with one alteration. 33.56 g or 0.76 mole of ethylene oxide were now used in place of 35.24 g or 0.8 mole of ethylene oxide, i.e., a 5% deficit of ethylene oxide. The THEEDA yield was 90.5% and in particular a relatively large amount of tri-HEEDA was produced as a by-product.

COMPARATIVE EXAMPLE 9

Example 5 was repeated with one alteration. The alteration was that no solvent was used at all. The THEEDA yield was 89.4% and in particular relatively large amounts of penta-HEEDA and hexa-HEEDA were produced as by-products.

We claim:

1. A process for the production of N,N,N',N'-tetra-(2-hydroxyethyl)-ethylene diamine by reacting ethylene diamine with ethylene oxide in a solvent, characterised in that ethylene diamine is reacted with ethylene oxide in the absence of water in one or more saturated $C_3$–$C_9$ alcohols at a temperature from 120 to 220° C. and at a pressure from 2 to 60 bar in a molar ratio of 1:4.

2. A process in accordance with claim 1, characterised in that the conversion is carried out in isopropanol.

3. A process in accordance with claim 1, characterised in that the conversion is carried out in isomeric $C_7$–$C_9$ alcohol mixtures or $C_8$ alcohol mixtures or $C_9$ alcohol mixtures.

4. A process in accordance with claim 1, characterised in that the conversion is carried out at a temperature from 140 to 180° C.

5. A process in accordance with claim 1, characterised in that the ethylene oxide is added to the submitted $C_3$–$C_9$ alcohol or alcohols and ethylene diamine within a period from 5 to 60 minutes.

6. A process in accordance with claim 5, characterised in that the ethylene oxide is added within a period from 15 to 25 minutes.

7. A process in accordance with claim 1, characterised in that the amount of saturated $C_3$–$C_9$ alcohol is selected so that the concentration of the end product is from 5 to 60% after conversion.

8. A process in accordance with claim 7, characterised in that the concentration of the end product is from 20 to 40% after conversion.

9. A process in accordance with claim 2, characterised in that the conversion is carried out at a temperature from 140 to 180° C.

10. A process in accordance with claim 3, characterised in that the conversion is carried out at a temperature from 140 to 180° C.

11. A process in accordance with claim 2, characterised in that the ethylene oxide is added to the submitted $C_3$–$C_9$ alcohol or alochols and ethylene diamine within a period from 5 to 60 minutes.

12. A process in accordance with claim 3, characterised in that the ethylene oxide is added to the submitted $C_3$–$C_9$ alcohol or alochols and ethylene diamine within a period from 5 to 60 minutes.

13. A process in accordance with claim 4, characterised in that the ethylene oxide is added to the submitted $C_3$–$C_9$ alcohol or alochols and ethylene diamine within a period from 5 to 60 minutes.

14. A process in accordance with claim 2, characterised in that the amount of saturated $C_3$–$C_9$ alcohol is selected so that the concentration of the end product is from 5 to 60% after conversion.

15. A process in accordance with claim 3, characterised in that the amount of saturated $C_3$–$C_9$ alcohol is selected so that the concentration of the end product is from 5 to 60% after conversion.

16. A process in accordance with claim 4, characterised in that the amount of saturated $C_3$–$C_9$ alcohol is selected so that the concentration of the end product is from 60% after conversion.

17. A process in accordance with claim 5, characterised in that the amour saturated $C_3$–$C_9$ alcohol is selected so that the concentration of the end product is from 60% after conversion.

18. A process in accordance with claim 6, characterised in that the amount of saturated $C_3$–$C_9$ alcohol is selected so that the concentration of the end product is from 5 to 60% after conversion.

* * * * *

UNITED STATES PATENT AND TRADEMARK OFFICE
CERTIFICATE OF CORRECTION

PATENT NO.   : 6,222,075 B1            Page 1 of 1
DATED        : April 24, 2001
INVENTOR(S)  : Klaus Ihrig; Manfred Bergfeld and Christian Blaufelder It is certified that error appears in the above-identified patent and that said Letters Patent is hereby corrected as shown below:

Title page,
Item [54], line 2, after "N' " (second occurrence), delete ",".

Column 1,
Line 45, change "FIG. 1 shows" to -- FIGS. 1A-1N show --.

Column 8,
Line 53, after "from" insert -- 5 to --;
Line 56, change "amour" to -- amount --; and
Line 57, after "from" insert -- 5 to --.

Signed and Sealed this

Eighteenth Day of December, 2001

Attest:

Attesting Officer

JAMES E. ROGAN
*Director of the United States Patent and Trademark Office*